United States Patent [19]

D'Silva

[11] 4,081,454

[45] Mar. 28, 1978

[54] CARBAMIC PESTICIDAL COMPOSITIONS

[75] Inventor: Themistocles Damasceno Joaquim D'Silva, S. Charleston, W. Va.

[73] Assignee: Union Carbide Corporation, New York, N.Y.

[21] Appl. No.: 688,221

[22] Filed: May 20, 1976

Related U.S. Application Data

[62] Division of Ser. No. 483,882, Jun. 27, 1974, Pat. No. 4,029,688.

[51] Int. Cl.$^2$ .......................... A01N 9/06; A01N 9/20
[52] U.S. Cl. .................................... 424/304; 424/226
[58] Field of Search ............................ 424/304, 226; 260/465.4, 465 D, 464, 453 R

[56] References Cited

U.S. PATENT DOCUMENTS

| | | | |
|---|---|---|---|
| 3,466,316 | 9/1969 | Payne, Jr. et al. | 260/465.4 |
| 3,483,246 | 12/1969 | Kaufman | 260/465 D |
| 3,522,287 | 7/1970 | Donninger et al. | 260/465.4 |
| 3,576,834 | 4/1971 | Buchanan | 260/465 D |
| 3,621,049 | 11/1971 | Addor et al. | 260/465.4 |
| 3,625,987 | 12/1971 | Hubele | 260/465.4 |
| 3,755,403 | 8/1973 | Bellina | 260/465.4 |
| 3,780,085 | 12/1973 | Engelhart | 260/465.4 |
| 3,803,320 | 4/1974 | Brechbuhler et al. | 260/465.4 |
| 3,890,386 | 6/1975 | Kuhle et al. | 260/465.5 R |
| 3,939,192 | 2/1976 | Kuhle et al. | 260/465.4 |

*Primary Examiner*—Albert T. Meyers
*Assistant Examiner*—D. W. Robinson
*Attorney, Agent, or Firm*—Richard C. Stewart

[57] ABSTRACT

N-haloalkanesulfenylcarbamoyloxime compositions have been found to have exceptional miticidal and insecticidal activity.

15 Claims, No Drawings

CARBAMIC PESTICIDAL COMPOSITIONS

This application is a division of my copending U.S. application Ser. No. 483,882, filed June 27, 1974, now U.S. Pat. No. 4,029,688.

This invention relates to novel compositions of matter and to their use in combating insects and mites.

The compounds which are employed as the active ingredients in the pesticidal compositions of this invention are new compounds corresponding to the following general formula:

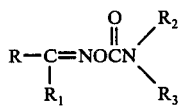

wherein:

R is:
A. lower alkyl;
B. lower alkyl substituted with one or more lower alkoxy, lower alkylthio, lower alkylsulfinyl, lower alkylsulfonyl, phenylthio, phenylsulfinyl, phenylsulfonyl or $R_4CON(R_5)$—, all of which may be substituted with one or more cyano, nitro, azido, chloro, bromo or fluoro substituents;

$R_1$ is:
A. hydrogen, chlorine, bromine, fluorine, cyano;
B. alkyl having from 1 to 4 carbon atoms, lower alkylthio, lower alkoxy, lower carboalkoxyalkylthio, lower alkylthioalkyl, all of which may either unsubstituted or substituted with one or more chloro, bromo, fluoro cyano or nitro groups.

$R_2$ is lower alkyl or lower alkyl substituted with one or more chloro, bromo, fluoro, nitro cyano, lower alkoxy or lower alkyl groups;

$R_3$ is perhalomethanesulfenyl or perhaloethanesulfenyl wherein the permissible halogen substituents are chloro, bromo or fluoro;

$R_4$ and $R_5$ are individually hydrogen or lower alkyl; with the proviso that
A. When R is alkyl, $R_1$ is substituted lower alkyl, substituted lower alkylthio, unsubstituted or substituted lower alkoxy, unsubstituted or substituted lower carboalkoxyalkylthio or unsubstituted or substituted lower alkylthioalkyl;
B. When $R_1$ is hydrogen, R is other than unsubstituted lower alkylthioalkyl; and
C. At least one of the groups R, $R_1$ and $R_2$ is a group including one or more cyano substituents when $R_1$ is other than cyano.

Compositions including these compounds as the active ingredient, are useful in combating insects and mites. In general, the compositions having the greatest degree of pesticidal activity are those in which the combined total number of aliphatic carbon atoms in the ennumerated substituents does not exceed about 10 carbon atoms.

The preferred compositions of this invention are those in which $R_2$ is methyl and $R_3$ perhalomethanesulfenyl.

It will be appreciated that the active compounds of this invention will exist in at least two isomeric forms. In the "syn" configuration, the oxygen atoms of the oximino function is on the same side of the oximino double bond as the R substituent in the generic formula set forth above while in the "anti" configuration, the oxygen atom is on the opposite side of the oximino function. Both isomers are within the scope of our invention, however the syn isomers are preferred due to their greater biological activity.

The novel compounds of this invention in comparison to the corresponding N-methylcarbamate compounds, some of which are well known insecticides, have been found to possess essentially equivalent insecticidal and miticidal activity although in some cases enhanced activity against particular pests have been observed. Surprisingly, however, the compounds of this invention demonstrate a sharp reduction in mammalian toxicity as compared to the N-methyl compounds. In addition nearly all of the novel compositions of this invention are quite stable under normal conditions and can be stored for long periods of time without appreciable loss or reduction in biological activity. This is to be contrasted with many of the corresponding N-methyl carbamate compositions which are relatively unstable and can not be stored for any appreciable length of time and as such are not useful pesticides because of practical considerations.

Compositions which exhibit the greatest stability, and generally enhanced pesticidal activity are those in which the cumulative sigma* value of the groups R and $R_1$ of the active compound is at least 1.1.

This problem of instability is particularly acute in the case of compounds of the type described above wherein $R_1$ is hydrogen if there is not present a relatively strong electron withdrawing function in the R substituent. Certain compounds, such as those in which $R_1$ is hydrogen and R is alkylthio are unstable despite the relatively strong electron withdrawing character of the alkylthio substituent. These compounds are not included within the scope of the generic formula as defined above.

The active compounds of this invention can be prepared conveniently in accordance with the following general reaction scheme:

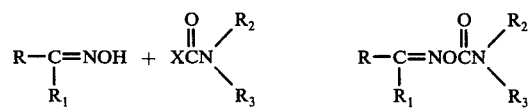

where R, $R_1$, $R_2$ and $R_3$ are as described above and where X is either chlorine or fluorine.

The oxime precursors used in the preparation of the active compounds of this invention can be prepared by conventional means as for example by the methods described in U.S. Pat. Nos. 3,217,036, 3,217,037, 3,400,153, 3,536,760 and 3,576,834.

The carbamic acid fluoride precursor compounds can be prepared by the method described in U.S. Pat. No. 3,769,471. The carbamic acid chloride compounds can be prepared by the method described in Belgium Pat. No. 796,646.

The reaction between the oxime compound and the carbamic acid halid compound is preferably carried out in an aprotic solvent and in the presence of a base. The preferred base materials are tertiary amines and alkaline earth bases. Yields obtained by this reaction are generally quantitative.

The following specific examples are presented to more particularly illustrate the manner in which the active compounds of this invention may be prepared.

EXAMPLE I

To a solution of 2.26 g (0.0111 m) N-methyl-N-trichloromethanesulfenylcarbamyl fluoride and 1.29 (0.011 m) 2-methyl-2-cyanopropionaldehydeoxime in 75 ml dioxane was added dropwise with stirring 1.28 g (0.013 m) triethylamine. The spontaneous exotherm raised the temperature from 23° to 29° C. After stirring for an additional period of 0.5 hr at ambient temperature, the reaction mixture was quenched with 300 ml of water. The product was extracted into ethylene acetate and the resulting solution was dried over magnesium sulfate and concentrated to a residual oil which crystallized from isopropyl ether to yield 2.0 g of the desired product 2-methyl-2-cyanopropionaldehyde-(N-methyl-N-trichloromethanesulfenylcarbamoyl)oxime mp 105°-107° C. Recrystallization raised the mp to 111°-113° C.

Analysis - Calcd. for $C_8H_{10}N_3O_2Cl_3S$: C, 30.16; H, 3.16; N, 13.19 Found: C, 30.15; H, 3.29; N, 13.36

EXAMPLE II

To a solution of 1.1 g (0.008 m) 1-(2-cyanoethylthio)acetaldoxime, and 1.8 g (0.008 m) N-methyl-N-(trichloromethanesulfenylcarbamoyl) fluoride in 50 ml of dioxane was added dropwise with stirring at 28°-30° C, 0.9 g of triethylamine. After stirring overnight at ambient temperature, the reaction mixture was poured in 500 ml of water and stirred for 10 minutes. The precipitated solid was washed with water and dried. On recrystallization from isopropanol it yielded 1.1 g of 1-(2-cyanoethylthio)acetaldehyde-(N-methyl-N-trichloromethanesulfenylcarbamoyl)oxime, mp 136°-138° C.

The following compositions in addition to those described in the above examples are illustrative of the new compositions of this invention:

2-Phenylthio-1-cyanoacetaldehyde O-(N-methyl-N-trichloromethanesulfenylcarbamoyl)oxime.

1-(2-Cyanopropylthio)acetaldehyde O-(N-methyl-N-trichloromethanesulfenylcarbamoyl)oxime.

1-(2-Cyanomethylthio)acetaldehyde O-(N-methyl-N-trichloromethanesulfenylcarbamoyl)oxime.

2-Cyano-2-methyl-1-(2-cyanoethylthio)propionaldehyde O-(N-methyl-N-trichloromethanesulfenylcarbamoyl)oxime.

2-Nitro-2-methyl-1-(2-cyanoethylthio)propionaldehyde O-(N-methyl-N-trichloromethanesulfenylcarbamoyl)oxime.

2-Methyl-2-cyanopropionaldehyde O-(N-methyl-N-trichloromethanesulfenylcarbamoyl)oxime.

3-Methyl-3-cyanobutanone-2O-(N-methyl-N-trichloromethanesulfenylcarbamoyl)oxime. 3-Cyanobutanone-2 O-(N-methyl-N-trichloromethanesulfenylcarbamoyl)oxime.

2-Methyl-2-cyanopropionaldehyde O -(N-methyl-N-trifluoromethanesulfenylcarbamoyl)oxime.

2-Methyl-2-cyanopropionaldehyde O-(N-methyl-N-fluorodichloromethanesulfenylcarbamoyl)oxime.

2-Methyl-2-(cyanoethyl)thiopropionaldehyde O-(N-methyl-N-trichloromethanesulfenylcarbamoyl)oxime.

2-Methyl-2-methoxy-1-cyanopropionaldehyde O-(N-methyl-N-trichloromethanesulfenylcarbamoyl)oxime.

2-Methyl-2-methylthio-1-cyanopropionaldehyde O-(N-methyl-N-trichloromethanesulfenylcarbamoyl)oxime.

2-Cyano-2-methyl-1-methylthiopropionaldehyde O-(N-methyl-N-trichloromethanesulfenylcarbamoyl)oxime.

1-(2-Cyanoethylthio)acetaldehyde O-(N-methyl-N-trichloromethanesulfenylcarbamoyl)oxime.

1-(2-cyanoethylthio)acetaldehyde O-(N-methyl-N-trifluoromethanesulfenylcarbamoyl)oxime.

1-(2-cyanoethylthio)acetaldehyde O-(N-methyl-N-fluorodichloromethanesulfenylcarbamoyl)oxime.

2-Methyl-2-cyanopropionaldehyde O-[N-(2-chloroethyl)-N-trichloromethanesulfenylcarbamoyl]oxime.

2-Methyl-2-cyanopropionaldehyde O-[N-(n-propyl)-N-dichlorofluoromethanesulfenylcarbamoyl]oxime.

2-Methyl-2-cyanopropionaldehyde O-[N-(2-nitroethyl)-N-trichloromethanesulfenylcarbamoyl]oxime 2-Methyl-2-cyanopropionaldehyde O-(N-cyanomethyl-N-trichloromethanesulfenylcarbamoyl)oxime.

2-Methyl-2-cyanopropionaldehyde O-(N-vinyl-N-trichloromethanesulfenylcarbamoyl)oxime 2-Methyl-2-cyanopropionaldehyde O-(N-benzyl-N-trichloromethanesulfenylcarbamoyl)oxime 2-Methyl-2-cyanopropionaldehyde O-(N-phenyl-N-trichloromethanesulfenylcarbamoyl)oxime 2-Methyl-2-cyanopropionaldehyde O-[N-(4-chlorophenyl)-N-trichloromethanesulfenylcarbamoyl]

2-Methyl-2-cyanopropionaldehyde O-[N-(4-methoxyphenyl)-N-trichloromethanesuflenylcarbamoyl]oxime Selected species of the new compounds were evaluated to determine their pesticidal activity against mites, nematodes and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65°-70° F. and 50-70 percent relative humidity, constituted the test insects. For testing purposes, the number of aphids per pot was standardized to 100-150 by trimming plants containing excess aphids.

The test compounds were formulated by diluting the stock suspension with water to give a suspension containing 500 parts of test compound per million parts of final formulation.

The potted plants (one pot per compound tested) infested with 100-150 aphids, were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Test

Larvae of the southern armyworm (*Prodenia eridania*, (Cram.)), reared on Tendergreen bean plants at a temperature of 80±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for 3 days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80±5° F. for 3 days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.), reared according to the specifications of the Chemical Specialities Manufacturing Association (Blue Book, McNair-Dorland Co., N.Y. 1954; pages 243-244, 261) under controlled conditions of 80±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for 24 hours, at a temperature of 80±5° F. and the relative humidity of 50±5 percent. Flies which showed no sign of movement on prodding were considered dead.

Mite Foliage Spray Test

Adults and numphal stages of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150–200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at 80±5 percent relative humidity for 6 days, after which a mortality count of motile forms was made. Microscopic examination for motile forms was made on the leaves of the test plants. Any individual which was capable of locomotion upon prodding was considered living.

MITE SYSTEMIC TEST

Systemic treatments were made by drenching 20 milliliters of the test compound formulation into the soil around the roots of bean plants growing in 2½ inch clay pots. These pots were held in 4 ounce wax paper containers to prevent cross-contamination and loss by leaching. The plants were 4 inches high at the time of treatment and had been infested with mites 24 hours previously. Subsequent steps for testing of the systemic miticidal activity were the same as those described above for the spray method of application.

NEMATOCIDE TEST

The test organism used was the infective migratory larvae of the root-knot nematode, *Meloidogyne incognita var. acrita,* reared in the greenhouse on roots of cucumber plants. Infected plants were removed from the culture, and the roots are chopped very finely. A small amount of this inoculum was added to a pint jar containing approximately 180 cc. of soil. The jars were capped and incubated for one week at room temperature. During this period eggs of the nematode were hatched, and the larval forms migrated into the soil.

Ten ml. of the test formulation were added to each of the two jars for each dosage tested. Following the addition of chemical, the jars were capped, and the contents thoroughly mixed on a ball mill for 5 minutes.

The test compounds were formulated by a standard procedure of solution in acetone addition of an emulsifier, and dilution with water. Primary screening tests were conducted at 3.33 m.g. of the test compound per jar.

The jars were left capped at room temperature for a period of 48 hours, and the contents then transferred to 3 inch pots. Subsequently, the pots were seeded to cucumber as an indicator crop and placed in the greenhouse where they were cared for in the normal fashion for approximately 3 weeks.

The cucumber plants were then taken from the pots, the soil removed from the roots, and the amount of galling visually rated.

In the tests described above, the pesticidal activity of the compounds against aphid, mite, Southern Armyworm, Bean Beetle, house fly and nematode was rated as follows:

A = excellent control
B = partial control
C = no control

Certain of these compositions were also evaluated to determine their peroral toxicity to mammals. The animal selected for this experiment was the rat. The test results obtained are expressed in terms of the number of milligrams of composition per kilogram of weight of the animal required to achieve a mortality rate of 50 percent ($LD_{50}$).

The results of these tests are set forth in Table I below: Dashes indicate no test conducted.

TABLE I

| Structure | m p c °C | Aphid | Mite (Spray) | Mite (Systemic) | Armyworm | Beetle | Fly | Nematode | Rat |
|---|---|---|---|---|---|---|---|---|---|
| NC—C(CH₃)(CH₃H)—C(=NOCN(SCCl₃)(CH₃))=O | 111–113 | A | A | A | A | A | A | C | — |
| NC—C(CH₃)(CH₃CH₃)—C(=NOCN(SCCl₃)(CH₃))=O | 74–76 | A | A | A | B | A | A | C | — |
| NC—C(CH₃)(CH₃H)—C(=NOCN(SCF₃)(CH₃))=O | 59–61 | A | A | — | A | A | A | A | — |
| CH₃—C(S(CH₂)₂CN)=NOCN(SCCl₃)(CH₃), C=O | 136–138 | A | A | — | A | A | A | C | 85.7 |

At higher dosage rates all of the above compositions may be expected to exhibit some activity against the various test species, however the data presented in Table I above clearly indicates a rather high degree of selectivity for some compositions and a broad spectrum of activity for others.

It will be understood that the insect species employed in the above tests are merely representative of a wide variety of pests that can be controlled by use of my compounds. These compounds demonstrate systemic as well as contact toxicity against insects and mites.

It should be noted that in addition to their insecticidal and miticidal activity, noteworthy nematocidal activity was also displayed by our compounds.

Comparison tests were conducted to assess the biological and chemical properties of certain representative species of the claimed invention in relation to their corresponding N-methyl carbamate compositions. The test procedures described above were employed in these experiments in order to determine the $LD_{50}$ (number of parts per million of active ingredients required to achieve fifty percent mortality of the insects tested) for each of the compositions tested. In the case of the aphid and mite tests a side by side comparison was made of the N-methyl carbamate composition versus the corresponding perhalomethylsulfenyl derivative. The results of these experiments are set forth in Table II below.

TABLE II
COMPARATIVE BIOLOGICAL ACTIVITY OF CERTAIN UNSUBSTITUTED N-METHYLCARBAMATE COMPOSITIONS N-METHYLCARBAMATE THEIR CORRESPONDING SULFENYLATED DERIVATIVES (LD₅₀ IN PPM)

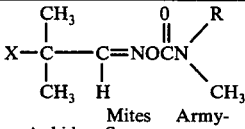

| R | X | Stability | Aphids | Mites Spray | Armyworm | Beetle | Housefly | Rat |
|---|---|---|---|---|---|---|---|---|
| H | CN | (unstable) | 12 | 40 | 55 | 65 | 3 | 9.5 |
| SCCl₃ | CN | (stable) | 23 | 23 | 50 | 45 | 7 | 28.3 |
| SCF₃ | CN | (stable) | 38 | 90 | 300 | 40 | 14 | — |
| H | — | (stable) | 8 | 8 | 5 | 25 | 2 | 7.7 |
| SCCl₃ | — | (stable) | 10 | 22 | 6 | 15 | 3 | 85.7 |

These experimental results clearly demonstrate the remarkable reduction in mammalian toxicity achieved with the present compositions in comparison to their corresponding N-methylcarbamate derivatives as well as their improved chemical stability.

The compounds contemplated in this invention may be applied as insecticides, miticides and nematocides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the aid of suitable surface active emulsifying and dispersing agents.

The choice of dispersing and emulsifyng agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects, mites and nematodes upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are now compatible with substantially any other constituents or the spray schedule, and they may be used in the soil, upon the seeds, or the roots of plants without injuring either the seeds or roots of plants. They may also be used in combination with other active ingredients such as miticides, insecticides and herbicides.

I claim:

1. An insecticide, miticide or nematocide composition comprising an acceptable carrier and an insecticidally, miticidally or nematocidally effective amount of a compound of the formula:

$$R-\underset{\underset{R_1}{|}}{C}=NOCNR_2R_3 \quad \overset{O}{\overset{\|}{}}$$

wherein

R is:
  A. lower alkyl;
  B. lower alkyl substituted with one or more lower alkoxy, lower alkylthio, lower alkylsulfinyl, lower alkylsulfonyl, phenylthio, phenylsulfinyl, phenylsulfonyl or R₄CON(R₅)-, all of which may be substituted with one or more cyano, nitro, azido, chloro, bromo or fluoro substituents;

R₁ is:
  A. hydrogen, chlorine, bromine, fluorine, cyano;
  B. alkyl having from 1 to 4 carbon atoms, lower alkylthio, lower alkoxy, lower carboalkoxyalkylthio, lower alkylthioalkyl, all of which may either be unsubstituted or substituted with one or more chloro, bromo, fluoro cyano or nitro groups;

R$_2$ is: lower alkyl or lower alkyl substituted with one or more chloro, bromo, fluoro, nitro, cyano, lower alkoxy or lower alkyl groups;

R$_3$ is: perhalomethanesulfenyl or perhaloethanesulfenyl wherein halogen substituents are chloro, bromo or fluoro;

R$_4$ and R$_5$ are individually hydrogen or lower alkyl; with the proviso that:
  A. When R is alkyl, R$_1$ is substituted lower alkyl, substituted lower alkylthio, unsubstituted or substituted lower alkoxy, unsubstituted or substituted lower carboalkoxyalkylthio or unsubstituted or substituted lower alkylthioalkyl;
  B. When R$_1$ is hydrogen, R is other than unsubstituted lower alkylthioalkyl; and
  C. At least one of the groups R, R$_1$ and R$_2$ is a group including one or more cyano substituents when R$_1$ is other than cyano.

2. The composition of claim 1 wherein the total number of aliphatic carbon atoms in the substituents R, R$_1$, R$_2$ and R$_3$ does not exceed about ten carbon atoms.

3. The composition of claim 1 wherein R$_2$ is lower alkyl and R$_3$ is perhalomethanesulfenyl.

4. The composition of claim 1 wherein the cumulative sigma* value of the groups R and R$_1$ is at least 1.1.

5. The composition of claim 1 wherein R$_1$ is lower alkyl.

6. The composition of claim 1 wherein R$_1$ is hydrogen.

7. The composition of claim 1 wherein R$_1$ is substituted lower alkylthio.

8. The composition of claim 1 wherein R is lower alkyl substituted with one or more lower alkylthio groups.

9. The composition of claim 1 wherein R is a nitro substituted lower alkyl.

10. The composition of claim 1 wherein R is a cyano subsituted lower alkyl.

11. The composition of claim 1 wherein R is lower alkylsulfinylalkyl.

12. The composition of claim 1 wherein R is lower alkylsulfonyl.

13. The composition of claim 1 wherein said compound is 2-Methyl-2-cyanopropionaldehyde (N-methyl-N-trichloromethanesulfenylcarbamoyl)oxime.

14. The composition of claim 1 wherein said compound is 1-(2-Cyanoethylthio)acetaldehyde O-(N-methyl-N-trichloromethanesulfenylcarbamoyl)oxime.

15. A method of controlling insects, mites and nematodes which comprises applying to said pests, an insecticidally, miticidally or nemato cidally effective amount of a compound of the formula:

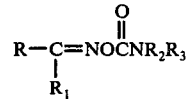

wherein
R is:
  A. lower alkyl;
  B. lower alkyl substituted with one or more lower alkoxy, lower alkylthio, lower alkylsulfinyl, lower alkylsulfonyl, phenylthio, phenylsulfinyl, phenylsulfonyl or R$_4$CON(R$_5$)—, all of which may be substituted with one or more cyano, nitro, azido, chloro, bromo or fluoro substituents;

R$_1$ is:
  A. hydrogen, chlorine, bromine, fluorine, cyano;
  B. alkyl having from 1 to 4 carbon atoms, lower alkylthio, alkoxy, carboalkoxyalkylthio, alkylthioalkyl, all of which may either be unsubstituted or substituted with one or more chloro, bromo, fluoro cyano or nitro groups, R$_2$ is: lower alkyl or lower alkyl substituted with one or more chloro, bromo, fluoro, nitro, cyano, lower alkoxy or lower alkyl group;

R$_3$ is: perhalomethanesulfenyl or perhaloethanesulfenyl wherein halogen substituents are chloro, bromo or fluoro;

R$_4$ and R$_5$ are individually hydrogen or lower alkyl; with the proviso that:
  A. When R is alkyl, R$_1$ is substituted lower alkyl, substituted lower alkylthio, unsubstituted or substituted lower alkoxy, unsubstituted or substituted lower carboalkoxyalkylthio or unsubstituted or substituted lower alkylthioalkyl;
  B. When R$_1$ is hydrogen, R is other than unsubstituted lower alkylthioalkyl; and
  C. At least one of the groups R, R$_1$ and R$_2$ is a group including one or more cyano substituents when R$_1$ is other than cyano.

* * * * *

UNITED STATES PATENT OFFICE

CERTIFICATE OF CORRECTION

Patent No. 4,081,454   Dated March 28, 1978

Inventor(s) Themistocles D.J. D'Silva

It is certified that error appears in the above-identified patent and that said Letters Patent are hereby corrected as shown below:

Column 3, line 52, "3-Methyl-3-cyanobutanone-2O-(N-methyl-N-tri-" should read -- 3-Methyl-3-cyanobutanone-2 O-(N-methyl-N-tri --.

Column 9, lines 1 through 5, which read,

" TABLE II

COMPARATIVE BIOLOGICAL ACTIVITY OF CERTAIN UNSUB-
N-METHYLCARBAMATE COMPOSITIONS
STITUTED N-METHYLCARBAMATE THEIR COR-
RESPONDING SULFENYLATED DERIVATES ($LD_{50}$ IN PPM "

should read,

-- TABLE II

COMPARATIVE BIOLOGICAL ACTIVITY OF CERTAIN UNSUBSTITUTED
N-METHYLCARBAMATE COMPOSITIONS AND THEIR CORRESPONDING
SULFENYLATED DERIVATIVES ($LD_{50}$ IN PPM) --

UNITED STATES PATENT OFFICE
CERTIFICATE OF CORRECTION

Patent No. 4,081,454  Dated March 28, 1978

Inventor(s) Themistocles D.J. D'Silva

It is certified that error appears in the above-identified patent and that said Letters Patent are hereby corrected as shown below:

Con. - Page 2.

Column 12, line 6, which reads " cidally, miticidally or nemato cidally effective amount" should read
-- cidally, miticidally or nematocidally effective amount --

Signed and Sealed this

Thirteenth Day of February 1979

[SEAL]

Attest:

RUTH C. MASON  
Attesting Officer

DONALD W. BANNER  
Commissioner of Patents and Trademarks